(12) United States Patent
Galante et al.

(10) Patent No.: US 8,048,406 B2
(45) Date of Patent: Nov. 1, 2011

(54) PERSONAL CARE PRODUCT

(75) Inventors: Cheryl L. Galante, Marshfield, MA (US); David L. Elliott, North Attleboro, MA (US); Iris Davis Gersten, Gaithersburg, MD (US); James L. Solan, Rockville, MD (US); Hermes van der Lee, Ashton, MD (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 09/784,488

(22) Filed: Feb. 15, 2001

(65) Prior Publication Data

US 2002/0155077 A1  Oct. 24, 2002

(51) Int. Cl.
*A61K 8/00* (2006.01)
*A61K 8/02* (2006.01)

(52) U.S. Cl. .......................... 424/65; 424/401

(58) Field of Classification Search .......... 424/400, 424/401, 65, 66, 68, DIG. 5
See application file for complete search history.

(56) References Cited

U.S. PATENT DOCUMENTS

| | | | |
|---|---|---|---|
| D27,864 S | 11/1897 | Blackman | |
| 692,481 A | 2/1902 | Robinson | |
| 964,422 A | 7/1910 | Hood | |
| 1,669,016 A | 5/1928 | O'Neil | |
| 1,791,359 A | 2/1931 | Henriksen | |
| 2,101,540 A | 12/1937 | Gullich | |
| 2,165,420 A | 7/1939 | Siefert | |
| 2,174,779 A | 10/1939 | Delorme | |
| 2,613,185 A | 10/1952 | Marshall | |
| 2,980,083 A | 1/1961 | Bell | |
| D201,229 S | 5/1965 | Burke | |
| 3,294,692 A | 12/1966 | Kelly et al. | |
| 3,479,429 A | 11/1969 | Morshauser et al. | |
| 4,120,948 A * | 10/1978 | Shelton | 424/401 |
| 4,202,879 A * | 5/1980 | Shelton | 424/66 |
| 4,393,643 A | 7/1983 | Fryar et al. | |
| 4,511,552 A | 4/1985 | Cox | |
| 4,524,062 A * | 6/1985 | Laba et al. | 424/65 |
| 4,578,207 A | 3/1986 | Holdt et al. | |
| 4,714,085 A | 12/1987 | Von Kleinsorgen | |
| 4,743,443 A | 5/1988 | Pisani et al. | |
| 4,786,449 A | 11/1988 | Smit | |
| 4,879,063 A | 11/1989 | Wood-Rethwill et al. | |
| 5,217,639 A | 6/1993 | Mottola | |
| D344,154 S | 2/1994 | Mottola | |
| 5,330,751 A | 7/1994 | Curtin et al. | |
| 5,417,964 A | 5/1995 | Carlson, Sr. et al. | |
| 5,538,161 A | 7/1996 | Koehler et al. | |
| 5,587,153 A | 12/1996 | Angelone, Jr. et al. | |
| 5,705,171 A | 1/1998 | Iovanni et al. | |
| 5,759,974 A | 6/1998 | Menke et al. | |
| 5,965,501 A | 10/1999 | Rattinger | |
| 5,968,489 A * | 10/1999 | Swaile et al. | 424/65 |
| D423,713 S | 4/2000 | Szekely | |
| D430,346 S | 8/2000 | van der Hagen | |
| 6,096,296 A | 8/2000 | Alflen et al. | |
| D443,951 S | 6/2001 | Look | |
| D444,264 S | 6/2001 | Look | |
| D444,265 S | 6/2001 | Look | |
| D444,593 S | 7/2001 | Look | |
| D444,913 S | 7/2001 | Look | |
| D446,356 S | 8/2001 | Look | |
| D446,606 S | 8/2001 | Look | |
| D446,607 S | 8/2001 | Look | |
| D449,405 S | 10/2001 | Gersten et al. | |
| D450,882 S | 11/2001 | Colwell et al. | |
| D454,227 S | 3/2002 | Look | |
| D454,228 S | 3/2002 | Look | |
| D454,229 S | 3/2002 | Look | |
| D454,414 S | 3/2002 | Look | |
| D454,661 S | 3/2002 | Look | |
| D454,662 S | 3/2002 | Look | |
| D454,663 S | 3/2002 | Look | |
| D454,664 S | 3/2002 | Look | |
| D454,665 S | 3/2002 | Look | |
| D454,666 S | 3/2002 | Look | |
| D454,983 S | 3/2002 | Look | |
| D454,984 S | 3/2002 | Look | |
| D454,985 S | 3/2002 | Look | |
| D456,560 S | 4/2002 | Gersten et al. | |
| D457,263 S | 5/2002 | Gersten et al. | |
| D457,264 S | 5/2002 | Gersten et al. | |
| 6,506,369 B2 | 1/2003 | Ambler et al. | |
| D469,923 S | 2/2003 | Gersten et al. | |
| D474,963 S | 5/2003 | Gersten et al. | |
| D474,964 S | 5/2003 | Gersten et al. | |
| 6,569,438 B1 * | 5/2003 | Banowski et al. | 424/401 |
| 6,695,510 B1 | 2/2004 | Look et al. | 401/68 |
| 2002/0041788 A1 | 4/2002 | Look et al. | |

FOREIGN PATENT DOCUMENTS

| | | |
|---|---|---|
| DE | 199 21 183 A1 | 11/2000 |
| FR | 977194 | 3/1951 |
| GB | 2014507 A | 2/1979 |
| GB | D2081820 | 7/1999 |
| WO | WO 99/23998 | 5/1999 |
| WO | WO 00/19861 | 4/2000 |
| WO | WO 91/91605 | 12/2001 |

OTHER PUBLICATIONS

The Body Shop Skin & Hair Care Products catalog holiday edition c 1995; p. 16 makeup indicated by arrows.
"Bac deo-stick", Nov. 15, 1999.

* cited by examiner

*Primary Examiner* — Sreeni Padmanabhan
*Assistant Examiner* — Layla Soroush
(74) *Attorney, Agent, or Firm* — David K. Benson; Paul A. Pappalardo

(57) ABSTRACT

A personal care product such as an antiperspirant product includes two portions having different compositions.

14 Claims, 6 Drawing Sheets

US 8,048,406 B2

PERSONAL CARE PRODUCT

TECHNICAL FIELD

This invention relates to personal care products.

BACKGROUND

Antiperspirant compositions are well known personal care products. The compositions come in a variety of forms and may be formulated, for example, into aerosols, pumps, sprays, liquids, roll-on, lotion, creams, and sticks (both hard and soft), etc.

There are various types of stick antiperspirant compositions. In one type, an antiperspirant salt is suspended in an anhydrous vehicle often including a solid water-insoluble wax. In a second type, an antiperspirant salt is dissolved in a liquid vehicle such as propylene glycol and gelled with a gelling agent such as dibenzylidene sorbitol. A third type includes an emulsion of an aqueous phase containing the antiperspirant salt and an oil phase containing, for example, a volatile silicone, fragrances, gellants, and other additives.

Cosmetic sticks including an antiperspirant portion and a deodorant portion are known in the art. See U.S. Pat. Nos. 4,202,879; 4,120,948; and 2,970,083.

SUMMARY

Generally, the invention relates to an antiperspirant and/or deodorant product including a container and a composition within the container. The composition has an application surface having two portions, each having a different composition. "Portion", as used herein, includes the section or sections of the application surface having the same composition; for example, two sections having the same composition but separated by a third section (for instance, a central stripe) having a different composition constitute a single "portion". Each section extends downwardly from the application surface and, preferably, extends at least 50%, and more preferably at least 80%, downwardly through the composition prior to first use. "Within the container", as used herein, means that at least part of the composition is within the container; for example, when the upper end of the composition including the application surface extends above the container the composition still is considered "within the container".

A composition including two different portions provides flexibility in designing the product. For example, the two portions may include different antiperspirant salts, or different quantities of the same antiperspirant salt. Alternatively, a multiple-portion product allows ingredients that generally should be kept apart to be incorporated into the same product. For example, one portion may include an antiperspirant salt while a second portion includes a fragrance that is incompatible with the antiperspirant salt. Moreover, one portion may be firmer or stronger than, and provide support for, the other portion.

The two-portion antiperspirant and/or deodorant product also provides the option of selecting from a number of aesthetically pleasing design choices. One portion can be clear and the other portion opaque. Moreover, the first portion and the second portion may have different colors, thus providing for a way to provide a composition including one or more stripes. "Different color", as used herein, includes different shades of a color. In addition, white and black are considered colors.

There are a number of different aspects of the invention.

In a first aspect, the first portion and the second portion each include an antiperspirant salt and each comprises at least 15%, and preferably at least 25%, of the application surface. Each portion can even comprise, for example, at least 40% of the application surface.

In a second aspect, the first portion and the second portion each includes at least 5.5 USP weight percent, and preferably 8 USP weight percent antiperspirant salt.

In a third aspect, the first portion and, optionally, the second portion includes an antiperspirant salt and the first portion and/or second portion is optically clear. Optically clear, as used herein, means that (1) the composition has a sufficient clarity to allow Font 8 text to be read through a 1 cm layer of the composition at normal light; and/or (2) the composition has an optical clarity better than 100 NTU (Nephelometric Turbidity Units) at 21° C. measured with an Orbeco-Hellige #965 Direct-Reading Turbidimeter. Preferred compositions have a sufficient clarity to allow the Font 8 text to be read through a 2 cm layer of the composition, and more preferred compositions may have a sufficient clarity to allow the Font 8 text to be read through a 5 cm layer of the composition. Preferred compositions also may have an optical clarity better than 70 NTU at 21° C., and more preferably less than 50 NTU at 21° C.

In a fourth aspect, both the first portion and the second portion include an antiperspirant salt and the application surface consists only of the two portions.

In a fifth aspect, the first portion includes a volatile silicone and the second portion includes a volatile silicone and an antiperspirant salt, and the first portion and the second portion each independently comprises at least 15% of the application surface.

In a sixth aspect, the first portion includes a volatile silicone and the second portion includes a volatile silicone and an antiperspirant salt, and the application surface consists only of the two portions.

In a seventh aspect, the first portion includes a high melting wax and the second portion includes a high melting wax and an antiperspirant salt, and the first portion and the second portion each independently comprises at least 15% of the application surface.

In an eighth aspect, the first portion includes a high melting wax and the second portion includes a high melting wax and an antiperspirant salt, and the application surface consists only of the two portions.

In a ninth aspect, the first portion includes from 0% to 10%, and preferably from 0% to 5%, by weight of a hydrophilic vehicle and a second portion including from 0% to 10%, and preferably from 0% to 5%, of a hydrophilic vehicle and an antiperspirant salt, and the first portion and the second portion each independently comprises at least 15% of the application surface. From "0%" includes 0%. "Hydrophilic vehicle", as used herein, includes monohydric alcohols including 2-6 carbon atoms such as ethanol, polyhydric alcohols having 3-6 carbon atoms and 2-6 hydroxyl groups such as propylene glycol, and water not bound to the antiperspirant salt.

In a tenth aspect, the first portion includes from 0% to 10% by weight of a hydrophilic vehicle and a second portion including from 0% to 10% of a hydrophilic vehicle and an antiperspirant salt, and the application surface consists only of the two portions.

In an eleventh aspect, the first portion includes at least 10% of the hydrophilic vehicle and the second portion includes at least 10% of a hydrophilic vehicle and an antiperspirant salt. Either or both portions may include, for example, 20% or even 50% of the hydrophilic vehicle by weight.

Other aspects of the invention include applying one of the antiperspirant products to the underarm in an amount effective to reduce perspiration, and making the antiperspirant product.

In another aspect, the invention features a product including a first portion and a second portion in which one or both portions includes a deodorant active ingredient and/or fragrance. In some embodiments, one or both portions include up to 5 USP weight percent of an antiperspirant active salt. In other embodiments, one or both portions may also include one or more of the components or other features of the antiperspirant products mentioned previously or described subsequently in the detailed description. The invention also features applying the deodorant product to the underarm.

Other features and advantages of the invention will be apparent from the description of the embodiment thereof, and from the claims.

DETAILED DESCRIPTION

Figure 1:
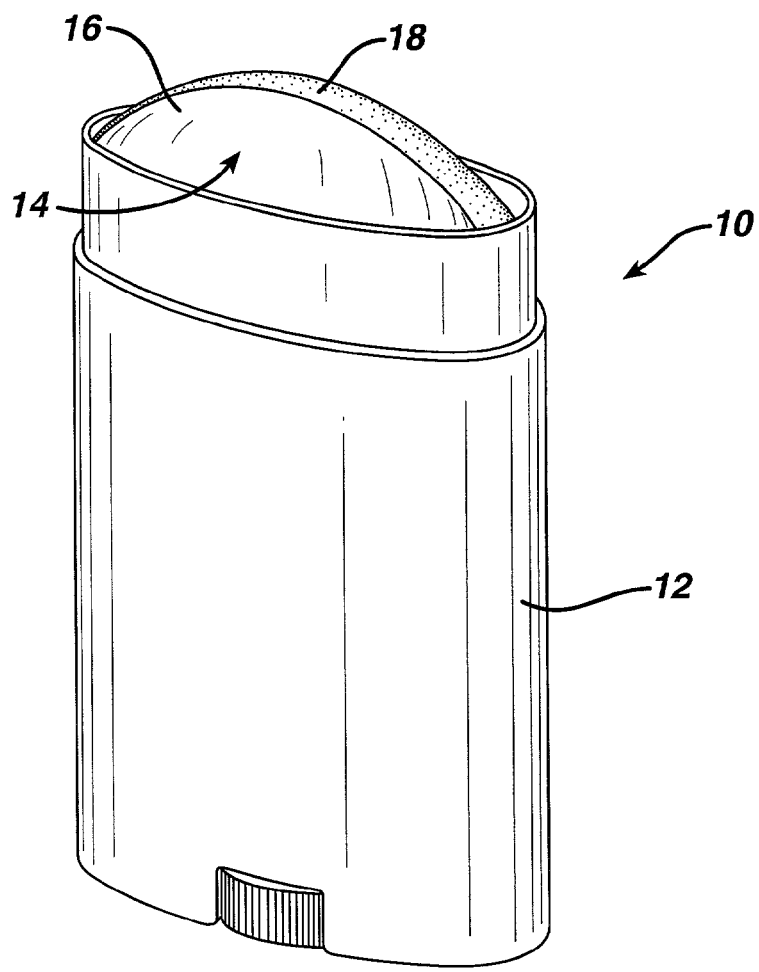
FIG. 1 is a perspective view of an antiperspirant product.
Figure 2:
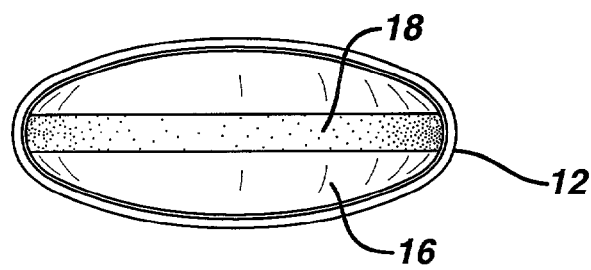
FIG. 2 is a top view of the antiperspirant product in FIG. 1.

Referring to FIGS. 1 and 2, an antiperspirant product 10 includes a container 12 and a composition within the container having domed application surface 14 for application to an underarm. The application surface can also be, for example, flat.

The composition includes portions 16 and 18 that together define application surface 14. Portion 18 is in the form of a stripe centrally running through and dividing portion 16. Portions 16 and 18 have different compositions and, in the embodiment shown, portion 18 has a different color than portion 16. For example, portion 18 may be dark blue, light blue, dark green, or light green, and portion 16 may be white, or vice versa. Because portions 16 and 18 have different colors, application surface 14 has a striped appearance. Portion 18 can have a width, for example, of at least 0.1 inch, and preferably between 0.2 inch and 0.5 inch. In product 10 portion 18 has a width of about 0.25 inch, which is between 25% and 35% of the application surface.

Figure 3:
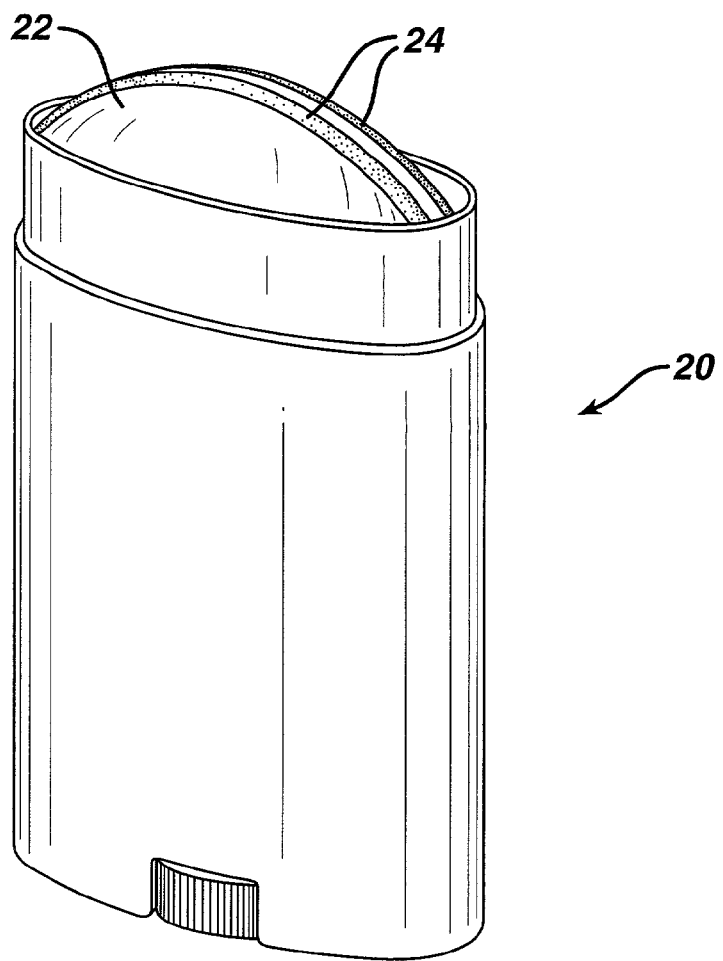
FIG. 3 is a perspective view of a second antiperspirant product.
Figure 4:
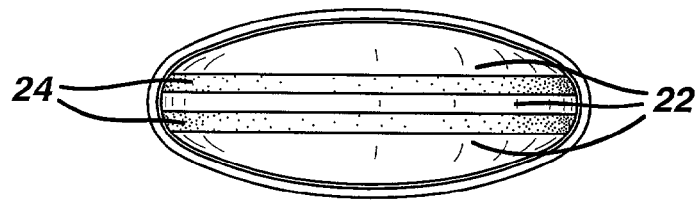
FIG. 4 is a top view of the antiperspirant product in FIG. 3.

FIGS. 3-10 are views of alternative antiperspirant products including two portions having different compositions. Referring to FIGS. 3 and 4, antiperspirant product 20 includes first portion 22 and second portion 24 in the form of a plurality (in this case two) strips extending through portion 22.

Figure 5:
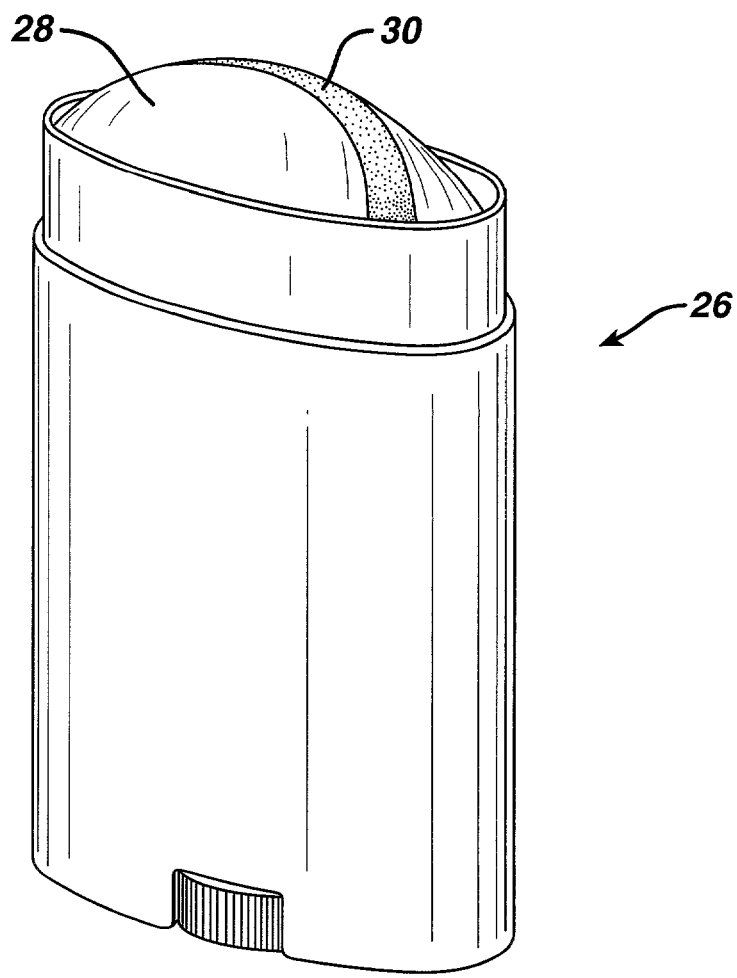
FIG. 5 is a perspective view of a third antiperspirant product.
Figure 6:
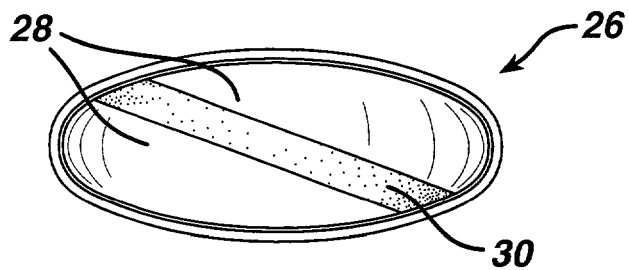
FIG. 6 is a top view of the antiperspirant product in FIG. 5.

Referring to FIGS. 5 and 6, antiperspirant product 26 includes first portion 28 and second portion 30 in the form of a generally diagonal stripe extending through portion 28.

Figure 7:
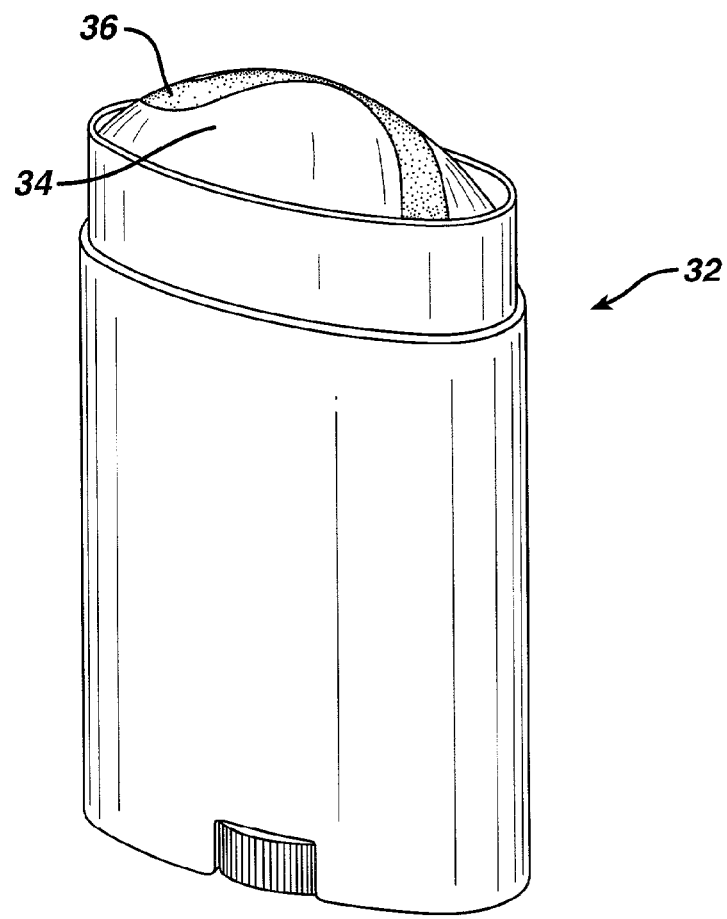
FIG. 7 is a perspective view of a fourth antiperspirant product.
Figure 8:
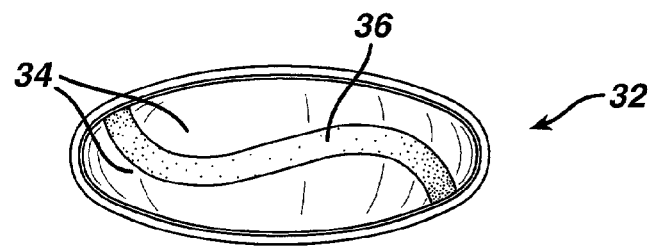
FIG. 8 is a top view of the antiperspirant product in FIG. 7.

Referring to FIGS. 7 and 8, antiperspirant product 32 includes first portion 34 and second portion 36 in the form of a wavy stripe extending (in this case generally diagonally) through portion 34.

The second portion in each of the above products extend through the full application surface of the product. In alternative embodiments the second portion does not quite extend to the edges of the application surface, at least at the initially exposed end of the product.

Figure 9:
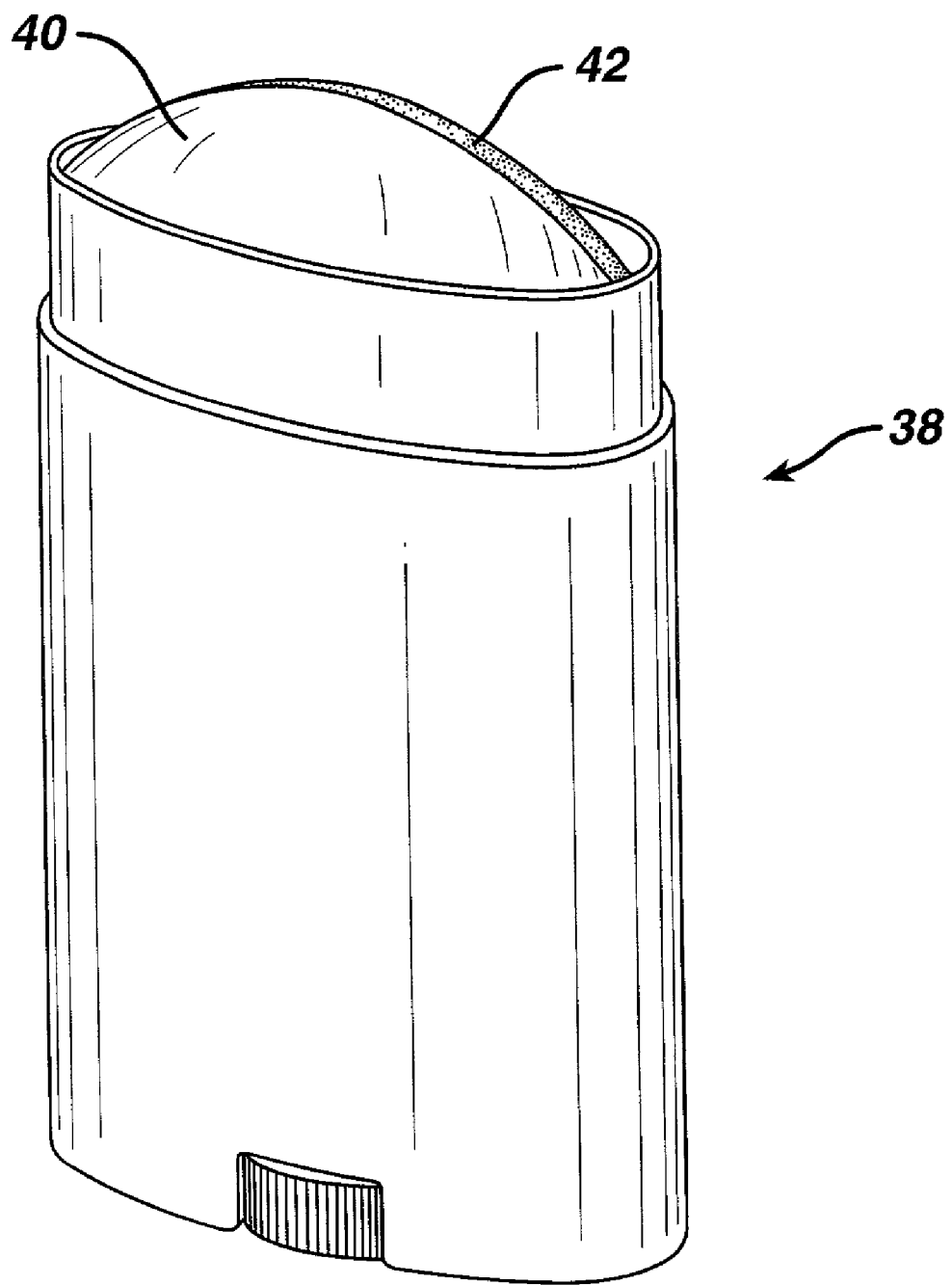
FIG. 9 is a perspective view of a fifth antiperspirant product.

Referring to FIG. 9, antiperspirant product 38 includes portion 40 and portion 42. Each portion comprises approximately half of the application surface of product 38.

Figure 10:
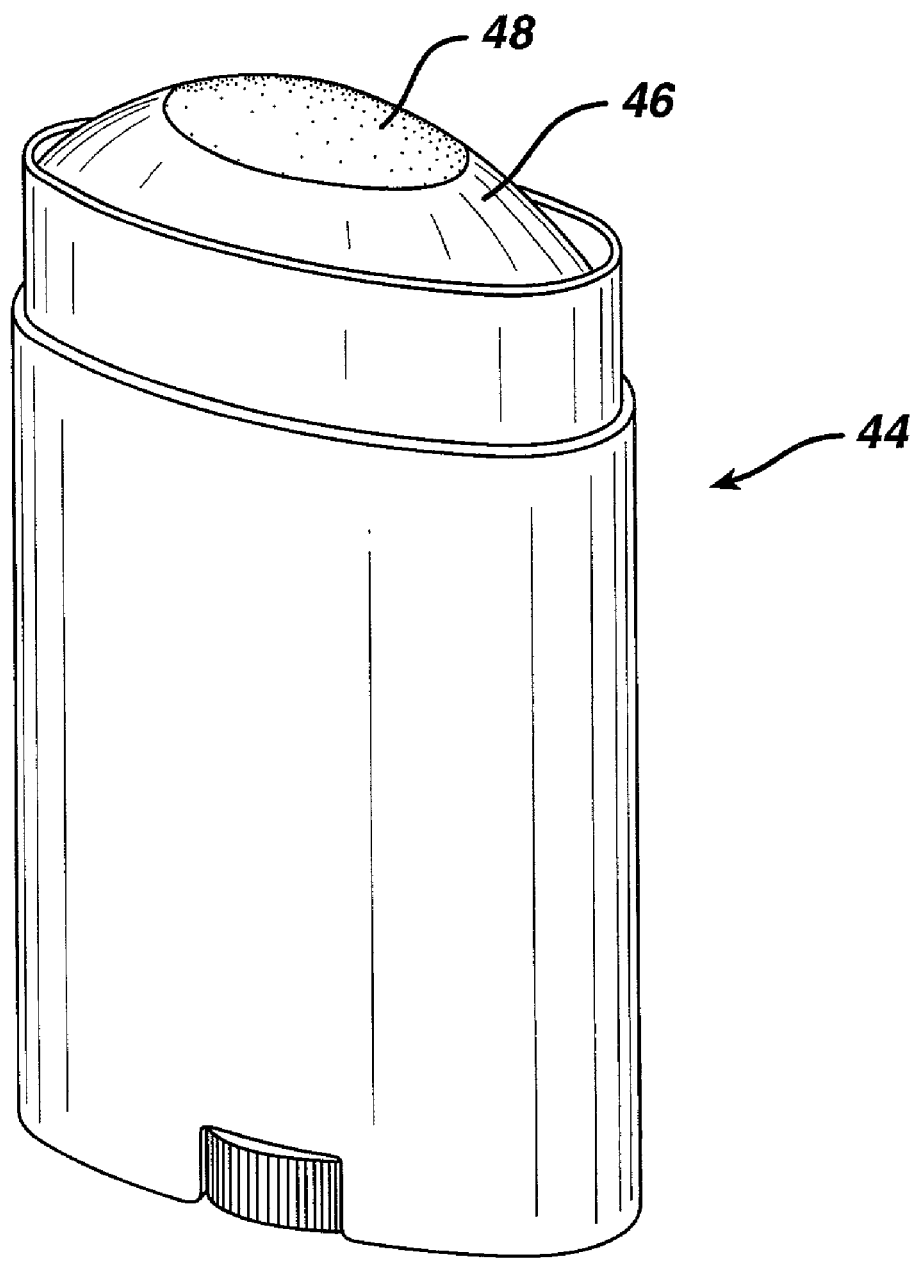
FIG. 10 is a perspective view of a sixth antiperspirant product.

Referring to FIG. 10, antiperspirant product 44 includes first portion 46 surrounding generally centrally located second portion 48.

One or both of the portions in the antiperspirant products discussed above may include an antiperspirant salt suspended in an anhydrous, hydrophobic vehicle including a volatile silicone and/or high melting component such as wax.

The preferred antiperspirant salts are aluminum salts and aluminum zirconium salts. Preferred aluminum salts are those having the general formula $Al_2(OH)_{6-a}X_a$ wherein X is Cl, Br, I, or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X is Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{4-pb}Y_b$ wherein Y is Cl, Br, I, $NO_3$, or $SO_4$, b is about 0.8 to 4, and p is the valence of Y. The zirconium salts also generally have some water of hydration associated with them, typically on the order of 1 to 7 moles per mole of salt. Preferably the zirconium salt is zirconium hydroxychloride of the formula $ZrO(OH)_{4-b}Cl_b$ wherein b is about 0.8 to 4, preferably about 1.0 to about 4. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "AZCH" herein. Generally, the aluminum-zirconium antiperspirant salts also contain a neutral amino acid such as glycine, typically in an amount to provide a Zr:Gly ratio of about 1:1 to 4:1.

The preferred ACH and AZCH salts are of the enhanced efficacy type. By "enhanced efficacy salt" is meant an antiperspirant salt which, when reconstituted as a 10% aqueous solution, produces an HPLC chromatogram (as described, for example, in U.S. Pat. No. 5,330,751, which is incorporated herein by reference) wherein at least 50%, preferably at least 70%, most preferably at least 80%, of the aluminum is contained in two successive peaks, conveniently labeled peaks 3 and 4, and wherein the ratio of the area under peak 4 to the area under peak 3 is at least 0.5, preferably at least 0.7, and more preferably at least 0.9 or higher. Particularly preferred, for example, are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH"' herein. Enhanced efficacy aluminum-zirconium chlorohydrate is referred to as "AZCH"' herein.

HPLC analysis means that chromatograms were obtained as follows: Salt solutions are evaluated for aluminum polymer distribution by HPLC at a concentration of about 10% Al or Al—Zr salt. If the solution to be analyzed is at a higher salt concentration, it is diluted with sufficient water to bring the salt concentration to about 10%. A 1.0 µL sample is pumped through a 4.6 mm×500 mm column packed with Nucleosil 100-5 silica (Keystone Scientific Inc.) using a 0.01M aqueous nitric acid solution as the eluent. The flow rate of the mobile phase was controlled at 0.5 mL/min with an LDC/Milton Roy ConstaMetric-II metering pump (ThermoQuest Inc). HPLC profiles were recorded and processed which has a computerized system that included the Millennium 32 Chromatography Manager software from the Waters Corp. A Waters 2410 differential refractometer was used as the refractive index detector. The HPLC profiles are read from left to right (higher to lower molecular weight). Following this technique, peak 3 typically appears at a retention time of 11.05-11.26 minutes (kd~0.58-0.62) and peak 4 typically appears at a retention time of 11.91-12.16 minutes (kd~0.69-0.73). Naturally, of course, other HPLC techniques which use different column materials, eluents and flow rates can be used provided that they sufficiently resolve peaks 3 and 4 with an acceptable degree of precision (i.e. the technique must be capable of resolving the Al into at least four distinct peaks). Obviously, such other techniques may place peaks 3 and 4 at different retention times from those given above.

An alternative enhanced efficacy antiperspirant salt are those described in U.S. Ser. No. 09/696,271, filed on Oct. 25, 2000, which has been assigned to the same assignee as the present application and is hereby incorporated by reference. Examples of these salts are aluminum-zirconium tetrachlochlorohydrate or aluminum-zirconium octochlorohydrate with an HPLC peak 5 area content of at least 45%. These enhanced efficacy salts will be referred to as "$E^5AZCH$"" herein.

In this application, weight percent (USP) of antiperspirant salt is calculated as anhydrous weight percent in accordance with the U.S.P. method. This calculation excludes any bound water and glycine. For aluminum chlorohydrate and aluminum-zirconium chlorohydrate, the calculation is as follows:

$$\%ACH = \%Al[26.98x + 17.01(3x-1) + 35.45]/26.98x$$
where $x = Al/Cl$ ratio;

$$\%AZCH = \%Al\{26.98y + 92.97 + 17.01[3y + 4 - (y+1)/z] + 35.45(y+1)/z\}/26.98y$$

where $y = Al/Zr$ ratio and $z = metal/Cl$ ratio.

For reference purposes, calculation of antiperspirant salt weight percent in accordance with the U.S.P. method compares to the previously used standard industry method is as follows: 50% ACH (std.)=40.8% (USP); 50% AZCH (std)=38.5% USP.

A portion or both portions of the antiperspirant composition includes the antiperspirant salt in a perspiration reducing effective amount (typically at a concentration of about 3% to about 25% USP active, more typically about 8% to about 22% USP active).

The anhydrous, hydrophobic vehicle comprises about 60% to 95%, preferably about 70% to 90%, of a portion or the portions of the antiperspirant composition. The vehicle generally includes one or more high melting components that melt at 70° C. or higher and/or a volatile silicone.

The high melting components may include any material suitable for use in an antiperspirant stick which melts at a temperature of about 70° C. or higher. Typical of such materials are the high melting point waxes. These include beeswax, spermaceti, carnauba, bayberry, candelilla, montan, ozokerite, ceresin, and paraffin waxes, semimicrocrystalline and microcrystalline waxes, hydrogenated jojoba oil, and hydrogenated castor oil (castor wax). The preferred wax is hydrogenated castor oil. Other suitable high melting components include various types of high melting gelling agents such as polyethylene-vinyl acetate copolymers, polyethylene homopolymers, 12-hydroxystearic acid, and substituted and unsubstituted dibenzylidene alditols. Typically, the high melting components comprise about 1 to 25%, preferably about 2 to 15%, of the composition.

Volatile silicones include the cyclic polydimethylsiloxanes, also known as cyclomethicones, which have from about 3 to about 6 silicon atoms, and the linear polydimethylsiloxanes, also known as dimethicones, which have from about 2 to about 9 silicon atoms. The linear volatile silicones generally have viscosities of less than about 5 centistokes at 25° C. while the cyclic volatile silicones have viscosities under 10 centistokes; an example is DC 200, which is available from Dow Corning Corp. "Volatile" means that the material has a measurable vapor pressure at room temperature. Cyclomethicones include DC 245, DC 344, and DC 345, all of which are also available from Dow Corning Corporation. Volatile silicones are described further in U.S. Ser. No. 09/672,350, filed Sep. 28, 2000, which is assigned to the same assignee as the present application and is hereby incorporated by reference.

Other components may include, for example, non-volatile silicones, polyhydric alcohols having 3-6 carbon atoms and 2-6 hydroxy groups, fatty alcohols having from 12 to 24 carbon atoms, fatty alcohol esters, fatty acid esters, fatty amides, non-volatile paraffinic hydrocarbons, polyethylene glycols, polypropylene glycols, polyethylene and/or polypropylene glycol ethers of C4-20 alcohols, polyethylene and/or polypropylene glycol esters of fatty acids, and mixtures thereof. The term "fatty" is intended to include hydrocarbon chains of about 8 to 30 carbon atoms, preferably about 12 to 18 carbon atoms.

Non-volatile silicones include polyalkylsiloxanes, polyalkylaryl siloxanes, and polyethersiloxanes with viscosities of about 5 to about 100,000 centistokes at 25° C., polymethylphenylsiloxanes with viscosities of about 15 to about 65 centistokes, and polyoxyallkylene ether dimethylsiloxane copolymers with viscosities of about 1200 to about 1500 centistokes.

Useful polyhydric alcohols include propylene glycol, butylenes glycol, dipropylene glycol and hexylene glycol. Fatty alcohols include stearyl alcohol, cetyl alcohol, myristyl alcohol, oleyl alcohol, and lauryl alcohol. Fatty alcohol esters include $C_{12-15}$ alcohols benzoate, myristyl lactate, cetyl acetate, and myristyl octanoate. Fatty acid esters include isopropyl palmitate, myristyl myristate, and glyceryl monostearate. Fatty amides include stearamide MEA, stearamide MEA-stearate, lauramide DEA, and myristamide MIPA.

Non-volatile paraffinic hydrocarbons include mineral oils and branched chain hydrocarbons with about 16 to 68, preferably about 20 to 40, carbon atoms. A preferred material is hydrogenated polyisobutene with about 24 carbon atoms. Suitable polyethylene glycols and polypropylene glycols will typically have molecular weights of about 500 to 6000, such as PEG-10, PEG-40, PEG-150 and PPG-20, often added as rheology modifiers to alter product appearance or sensory attributes.

Polyethylene and/or polypropylene glycol ethers or $C_{4-20}$ alcohols include PPG-10 Butanediol, PPG-14 Butyl Ether, PPG-5-Buteth-7, PPG-3-Isostearth-9, PPG-3-Myreth-3, Oleth-10, and Steareth-20. Polyethylene and/or polypropylene glycol esters of fatty acids include PEG-8 Distearate, PEG-10 Dioleate, and PPG-26 Oleate. These are generally added to give emollient properties.

The above list of materials is by way of example only and is not intended to be a comprehensive list of all potential antiperspirant stick components. Other low melting waxes, non-volatile emollients and suitable components are readily identifiable to those skilled in the art. Of course, other ingredients such as colloidal silicas, particulate polyolefins, talcum materials, fragrances, colorants and preservatives may also be included as desired. For example, the composition may include up to about 10% fragrance or about 2% colorant by weight.

Deodorant active ingredients may also be included as desired. A suitable deodorant active is any agent that inhibits, suppresses, masks or neutralizes malodor. These may include (1) antimicrobial or bactericidal agents which kill the bacteria responsible for malodor production, (2) agents which inhibit or suppress or interfere with the bacterial enzymatic pathway that produces malodor, and (3) agents which mask or absorb or neutralize malodor. Fragrances are not considered deodorant active ingredients within the meaning of this application. Examples of deodorant actives include triclosan, triclocarban, usnic acid salts, zinc phenolsulfonate, b-chloro-D-alanine, D-cycloserine, aminooxyacetic acid, cyclodextrin, sodium bicarbonate. The composition generally may comprise, by weight, about 0.01% to about 10%, preferably about 0.1% to about 6%, deodorant active.

One or both of the portions in the antiperspirant products discussed previously may include the antiperspirant salt dissolved in a polyhydric alcohol liquid carrier like propylene glycol and gelled with a gelling agent such as dibenzylidene sorbitol. This is a preferred approach to providing a product in which one or both portions are clear. Compositions of this type are described in U.S. Pat. No. 5,705,171, which is incorporated by reference herein. A preferred composition as discussed in that patent, includes about 40% to about 95% of the liquid vehicle, about 0.1% to about 5% of the gelling agent, and about 0.5% to about 25% of the antiperspirant salt. About 0.05% to about 3% of a chelating agent may also be included to improve odor and clarity.

The preferred liquid vehicles include those discussed above and in particular the polyhydric alcohols comprising 3-6 carbon atoms and 2-6 hydroxyl groups.

The preferred gelling agents are dibenzylidene alditols. Examples include dibenzylidene sorbitol (DBS), dibenzylidene xylitol, and dibenzylidene ribitol. The aromatic rings in each benzylidene group may be unsubstituted or substituted, as described in U.S. Pat. No. 5,200,174, which is incorporated herein by reference. When substituted, it is preferred that the benzyl ring contain an electron withdrawing group at the meta position. Typical substituted compounds include di(meta-fluorobenzylidene) sorbitol and di(meta-chlorobenzylidene) sorbitol. The preferred gelling agent is dibenzylidene sorbitol (DBS).

The composition may also include one or more of other ingredients discussed previously.

One or both of the portions of the composition may be in the form of a water-in-oil emulsion comprised of an aqueous phase including the antiperspirant salt and an oil phase including a volatile silicone. This is an alternative approach for providing a product in which one or both portions are clear. Clarity is achieved by matching the refractive index of the water phase with the refractive index of the oil phase. Compositions of this type are described in U.S. Pat. No. 5,587,153, which is incorporated by reference herein.

The water phase may include water and other polar species such as the mono- and polyhydric alcohols including discussed previously. The water phase may comprise, for example, between about 70% and about 90% of the composition by weight.

The oil phase may include one or more of the volatile silicones and one or more of the non-volatile silicones discussed previously. The oil phase may comprise, for example, between about 10% and about 30% of the composition by weight.

The following are examples of antiperspirant products including two portions.

Example 1

An antiperspirant product having a central stripe (see FIGS. 1 and 2) had the following composition.

| Ingredient | Weight % |
|---|---|
| Outer portion: | |
| Volatile silicone (D4)[1] | 38.59 |
| AZCH" powder | 24.00[2] |
| Silica (R972)[3] | 0.72 |
| Silica (300)[4] | 0.18 |
| Stearyl alcohol | 20.00 |
| MP70 Castor wax[5] | 2.84 |
| Myristyl myristate | 1.92 |
| PPG-14 Butyl ether | 11.00 |
| Fragrance-1539[6] | 0.75 |
| Stripe portion: | |
| Volatile silicone (D4) | 37.49 |
| AZCH' powder | 19.00[7] |
| Silica (R972) | 0.72 |
| Silica (300) | 0.18 |
| Stearyl alcohol | 20.00 |
| MP70 Caster wax | 2.84 |
| Myristyl myristate | 1.92 |
| PPG-14 Butyl ether | 11.00 |
| Colorona Dark Blue[8] | 0.10 |
| Fragrance-1539 | 0.75 |
| InCap 1539[9] | 6.00 |

[1]Purchased from Dow Chemical (DC 245 fluid).
[2]USP wt. % = 18.3%.
[3]Purchased from Degussa Corporation.
[4]Purchased from Degussa Corporation.
[5]Modified castor oil purchased from CashChem.
[6]Fragrance purchased from Haarmann and Reimer.
[7]USP wt. % = 14.5%.
[8]Pigment/colorant, purchased from Rona, division of EM Chemicals.
[9]Encapsulated fragance purchased from Haarmann and Reimer.

The above product was prepared as follows. The outer portion of the product is prepared by mixing the first four components as a premix (the volatile silicone, the AZCH", and the two silicas) followed by a homogenization step. The stearyl alcohol, the MP70 castor wax, the myristyl myristate, and the PPG-14 butyl ether are heated to about 85° C. to form a molten homogeneous mix. The molten mix is cooled to about 70° C. The premix is then added to the mix while holding the temperature at between 65° C. and 70° C. The mix is then cooled to about 65° C., and the fragrance is added. The completed formulation is then cooled to about 54° C. and then poured into appropriate packaging.

The placement of the inner portion (to form the stripe) is achieved by either using a removable insert with the outer portion, or by coring the hardened outer portion to form a cavity for the inner portion. If the insert is used, it is removed after the outer portion has hardened to leave a cavity into which the inner portion formulation can be poured. Coring of the outer portion gives a similar result. An example of an insert is described in U.S. Ser. No. 09/784,493, filed Feb. 15, 2001, now U.S. Pat. No. 6,838,032, to issue on Jan. 4, 2005, which was filed on the same day as the present application, and is commonly owned with the present application, and is hereby incorporated by reference.

The inner portion is prepared similarly to the outer portion and then poured into the cavity to give the final product having a colored stripe. To the molten stearyl alcohol, MP70 castor wax, myristyl myristate, and PPG-14 butyl ether is added the homogenized premix of the volatile silicone, the AZCH", and the two silicas, holding the temperature between 65° C. and 70° C. The mix is then cooled to about 65° C., and the free oil fragrance, encapsulated fragrance, and pigment (Colorona Dark Blue) are added. The mix is cooled to about 54° C. and poured into the cavity (between the outer portion).

The cooled, hardened sticks resulting from this procedure have a white or off-white outer portion and a blue inner portion, with the outer portion having higher AP salt composition and free oil fragrance, and the inner portion having encapsulated and free oil fragrance and lower salt content.

An alternative procedure for preparing the antiperspirant product is described in U.S. Ser. No. 09/784,487, filed Feb. 15, 2001, now U.S. Pat. No. 6,723,269, issued Apr. 20, 2004, which was also filed on the same day as the present application, and is commonly owned with the present application, and is hereby incorporated by reference.

Example 2

A further example of an antiperspirant stick product illustrated in FIGS. 1 and 2 that include an outer clear portion and an inner clear blue portion was prepared. The antiperspirant stick included the following ingredients:

| Ingredient | Weight % |
|---|---|
| Outer Phase: | |
| Propylene glycol | 86.85 |
| AZCH' | 8.60[1] |
| Dibenzylidene sorbitol | 1.30 |
| Diisopropyl sebacate | 1.00 |
| Hydroxypropyl cellulose | 0.30 |
| Dimethicone copolyol | 0.25 |
| Tetrasodium EDTA | 0.20 |
| Fragrance | 1.50 |
| Inner Phase: | |
| Propylene glycol | 86.70 |
| AZCH' | 8.60[1] |
| Dibenzylidene sorbitol | 1.30 |
| Diisopropyl sebacate | 1.00 |
| Hydroxypropyl cellulose | 0.30 |
| Dimethicone copolyol | 0.25 |
| Tetrasodium EDTA | 0.30 |
| Fragrance | 1.50 |
| Colorona Dark Blue | 0.05 |

[1]USP wt. % = 8.6%.

Both the outer and inner portions were prepared using the procedure in U.S. Pat. No. 5,723,135, Examples 2 and 3, column 9, lines 1-50. The resulting product has transparent outer and inner portions with the inner portion tinted blue.

Example 3

A further example of an antiperspirant stick product illustrated with a clear inner stripe and a white outer portion can include the following ingredients:

| Ingredient | Weight % |
|---|---|
| Outer portion: | |
| Volatile silicone(D$_4$) | 38.49 |
| AZCH" | 24.00[1] |
| Silica (R972) | 0.72 |
| Silica (300) | 0.18 |
| Stearyl alcohol | 20.00 |
| MP70 castor wax | 2.84 |
| Myristyl myristate | 1.92 |
| PPG-14 Butyl ether | 11.00 |
| Fragrance-1571 | 0.85 |
| Inner portion: | |
| Propylene glycol | 86.85 |
| AZCH' | 8.60[2] |
| Dibenzylidene sorbitol | 1.30 |
| Diisopropyl stearate | 1.00 |
| Hydroxypropyl cellulose | 0.30 |
| Dimethicone copolyol | 0.25 |
| Tetrasodium EDTA | 0.20 |
| Fragrance | 1.50 |

[1]USP wt. % = 18.3%.
[2]USP wt. % = 8.6%.

The outer portion is prepared as in Example 1. The cavity is formed using either the removable insert or a coring device as in Example 1.

The inner portion is prepared as shown in U.S. Pat. No. 5,723,135, Examples 2 and 3 (column 9, lines 1-50). The inner portion is poured into the cavity in the outer portion to give the final product form.

The resulting product has an outer portion that is opaque, (white or off-white) and an inner portion that is transparent with a blue tint. The two portions have differing amounts of AZCH'.

Example 4

An antiperspirant product having a central stripe (see FIGS. 1 and 2) has the following composition. In this product, the fragrance (both free oil and encapsulated forms) is separated from the high efficacy salt. This provides good product performance and stability.

| Ingredient | Weight % |
|---|---|
| Outer portion: | |
| Volatile silicone (D4) | 39.34 |
| AZCH" powder (high peak 5 content) | 24.00[1] |
| Silica (Aerosil R972) | 0.72 |
| Silica (Aerosil 300) | 0.18 |
| Stearyl alcohol | 20.00 |
| MP70 Castor wax | 2.84 |
| Myristyl myristate | 1.92 |
| PPG-14 Butyl ether | 11.00 |
| Inner portion: | |
| Volatile silicone (D4) | 37.39 |
| AZCH' powder | 19.00[2] |
| Silica (Aerosil R972) | 0.72 |
| Silica (Aerosil 300) | 0.18 |
| Stearyl alcohol | 20.00 |
| MP70 Caster wax | 2.84 |
| Myristyl myristate | 1.92 |
| PPG-14 Butyl ether | 11.00 |
| Fragrance (free oil) | 0.85 |

| Ingredient | Weight % |
|---|---|
| Fragrance (encapsulated) | 6.00 |
| Colorona Dark Blue Pigment | 0.10 |

[1] USP wt. % = 17.5%.
[2] USP wt. % = 14.5%.

This product is prepared as in Example 1. The outer portion of the product is prepared by mixing the first four components as a premix (the volatile silicone, the AZCH", and the two silicas) followed by a homogenization step. The stearyl alcohol, the MP70 castor wax, the myristyl myristate, and the PPG-14 butyl ether are heated to about 85° C. to form a molten homogeneous mix. The molten mix is cooled to about 70° C. The premix is then added to the mix while holding the temperature at between 65° C. and 70° C. The mix is then cooled to about 65° C., and the fragrance is added. The completed formulation is then cooled to about 54° C. and then poured into appropriate packaging.

The placement of the inner portion (to form the stripe) is achieved by either using a removable insert with the outer portion, or by coring the hardened outer portion to form a cavity for the inner portion. If the insert is used, it is removed after the outer portion has hardened to leave a cavity into which the inner portion formulation can be poured. Coring of the outer portion gives a similar result. An example of an insert is described in U.S. Ser. No. 09/784,493 (now U.S. Pat. No. 6,838,032), which was filed on the same day as the present application and is commonly owned with the present application, and is hereby incorporated by reference.

The inner portion is prepared similarly to the outer portion and then poured into the cavity to give the final product having a colored stripe. To the molten stearyl alcohol, MP70 castor wax, myristyl myristate, and PPG-14 butyl ether is added the homogenized premix of the volatile silicone, the AZCH", and the two silicas, holding the temperature between 65° C. and 70° C. The mix is then cooled to about 65° C., and the free oil fragrance, encapsulated fragrance, and pigment (Colorona Dark Blue) are added. The mix is cooled to about 54° C. and poured into the cavity (between the outer portion).

The cooled, hardened sticks resulting from this procedure have a white or off-white outer portion and a blue inner portion, with the outer portion having higher AP salt composition and free oil fragrance, and the inner portion having encapsulated and free oil fragrance and lower salt content.

An alternative procedure for preparing the antiperspirant product is described in U.S. Ser. No. 09/784,487 (now U.S. Pat. No. 6,723,269), which was also filed on the same day as the present application and is commonly owned with the present application, and is hereby incorporated by reference.

Example 5

An antiperspirant product having a central stripe (see FIGS. 1 and 2) has the following composition. In this product, two fragrance types are used, with free oil in both portions and encapsulated fragrance in the inner portion to provide good deodorant benefit.

| Ingredient | Weight % |
|---|---|
| Outer Portion | |
| Volatile silicone($D_4$) | 38.49 |
| AZCH powder | 24.00[1] |
| Silica (Aerosil R972) | 0.72 |
| Silica (Aerosil 300) | 0.18 |
| Stearyl alcohol | 20.00 |
| MP70 castor wax | 2.84 |
| Myristyl myristate | 1.92 |
| PPG-14 Butyl ether | 11.00 |
| Fragrance (free oil) | 0.85 |
| Inner Portion | |
| Volatile silicone($D_4$) | 37.06 |
| AZCH powder | 19.50[2] |
| Silica (Aerosil R972) | 0.58 |
| Silica (Aerosil 300) | 0.15 |
| Stearyl alcohol | 20.00 |
| MP70 Castor Wax | 2.84 |
| Myristyl myristate | 1.92 |
| PPG-14 butyl ether | 11.00 |
| Fragrance (free oil) | 0.85 |
| Fragrance (encap.) | 6.00 |
| Colorona Dark Blue Pigment | 0.10 |

[1] USP wt. % = 18.3%.
[2] USP wt. % = 14.9%.

The product can be prepared as in Example 4.

Other embodiments are within the claims. For example, the composition may be a deodorant composition including two portions. Moreover, the composition may include three, four, or even five portions.

What is claimed is:

1. A product for underarm application, the product including an application surface that contacts the underarm during use of the product, the product comprising
    a container, and
    a first product portion having a first composition and a second product portion having a second composition, wherein one portion is firmer than, and provides support for, the other portion, wherein both the first composition and the second composition comprise an antiperspirant salt suspended in an anhydrous, hydrophobic vehicle including one or both of a volatile silicone and a wax having a melting temperature of at least 70 degrees C., and both the first composition and the second composition form part of the application surface.

2. The product of claim 1, wherein the second portion is in the form of a lengthwise-extending stripe extending approximately from a first end of the application surface to a second end of the application surface.

3. The product of claim 1, wherein the first portion and the second portion each independently comprise at least 15% of the application surface.

4. The product of claim 1, wherein both the first composition and the second composition further comprise up to 10% by weight hydrophilic vehicle.

5. A product for underarm application, the product including an application surface that contacts the underarm during use of the product, the product comprising
    a container, and
    a first product portion having a first composition and a second product portion having a second composition, wherein one portion is different in color and firmer than, and provides support for, the other portion, wherein both the first composition and the second composition comprise an antiperspirant salt suspended in an anhydrous, hydrophobic vehicle including one or both of a volatile silicone and a wax having a melting temperature of at least 70 degrees C., wherein, and both the first composition and the second composition form part of the application surface.

6. The product of claim 5, wherein either the first composition or the second composition is in the form of a lengthwise-extending stripe extending approximately from a first end of the application surface to a second end of the application surface.

7. The product of claim 5, wherein both the first composition and the second composition further comprise up to 10% by weight hydrophilic vehicle.

8. A product for underarm application, the product including an application surface that contacts the underarm during use of the product, the product comprising
 a container, and
 a first product portion having a first composition and a second product portion having a second composition, wherein one portion is different in color and firmer than, and provides support for, the other portion, wherein the first composition comprises more than 6 USP weight percent of an antiperspirant salt suspended in an anhydrous, hydrophobic vehicle including one or both of a volatile silicone and a wax having a melting temperature of at least 70 degrees C. and the second composition comprises less than 6 USP weight percent of an antiperspirant salt suspended in an anhydrous, hydrophobic vehicle including one or both of a volatile silicone and a wax having a melting temperature of at least 70 degrees C., the application surface consisting of the first composition and the second composition.

9. The product of claim 8, wherein the first composition or the second composition is in the form of a lengthwise-extending stripe extending approximately from a first end of the application surface to a second end of the application surface.

10. The product of claim 8, wherein the first composition comprises from at least 6 USP weight percent to 25 USP weight percent of the antiperspirant salt and the second portion comprises from at least 3 USP weight percent to 6 USP weight percent of the antiperspirant salt.

11. The product of claim 4, wherein the hydrophilic vehicle comprises a polyhydric alcohol.

12. The product of claim 7, wherein the hydrophilic vehicle comprises a polyhydric alcohol.

13. The product of claim 8, wherein both the first composition and the second composition further comprise up to 10 weight percent hydrophilic vehicle.

14. The product of claim 13, wherein the hydrophilic vehicle comprises a polyhydric alcohol.

\* \* \* \* \*